United States Patent [19]

Portner et al.

[11] 4,360,019

[45] Nov. 23, 1982

[54] IMPLANTABLE INFUSION DEVICE

[75] Inventors: Peer M. Portner, Kensington; Jal S. Jassawalla, San Francisco, both of Calif.

[73] Assignee: Andros Incorporated, Berkeley, Calif.

[21] Appl. No.: 135,219

[22] Filed: Mar. 31, 1980

Related U.S. Application Data

[63] Continuation-in-part of Ser. No. 15,927, Feb. 28, 1979, Pat. No. 4,265,241.

[51] Int. Cl.³ .............................................. A61M 7/00
[52] U.S. Cl. ............................ 128/213 R; 128/214 F
[58] Field of Search ................ 128/260, 214 F, 213 R

[56] References Cited

U.S. PATENT DOCUMENTS

| | | | |
|---|---|---|---|
| 3,923,060 | 12/1975 | Ellinwood | 128/260 |
| 4,193,397 | 3/1980 | Tucker et al. | 128/214 F X |
| 4,221,219 | 9/1980 | Tucker | 128/260 |
| 4,265,241 | 5/1981 | Portner et al. | 128/260 |

*Primary Examiner*—George J. Marlo
*Attorney, Agent, or Firm*—Fitch, Even, Tabin, Flannery & Welsh

[57] ABSTRACT

An infusion system is disclosed for delivering precisely regulated and variable dosages of drugs. The device includes a reservoir for containing the drug, a catheter for delivering drug to the body, and actuating means responsive to a signal applied externally of the body for initiating delivery of a precisely regulated dosage. The actuating means include; a solenoid driven miniature pump which is controlled by an implanted controller and driven by an implanted power source. The implanted controller provides a basal dosage rate which itself may be variable or constant and which may be altered by telemetry signals delivered from outside the body. In addition, the internal device is operable by an external unit which may be set at a different rate from that which the internal or implanted controller is set and which, in addition, provides power for operating the implanted device. The reservoir is maintained at zero gauge or slightly negative gauge pressure to prevent loss of the contents of the reservoir into the body in which the device is implanted in the event of a failure. A tube communicating between the reservoir and the catheter is bent around on itself in such a way as to prevent bubbles from entering the tube. The implanted power and control electronics may be overridden to provide power from an extra corporeal unit and is also programmable from the extra corporeal unit to adjust dosage rates. A bellows is used to maintain a constant pressure within the reservoir, and suitable plates are utilized to produce a capacitive signal indicating the volume remaining of the contents of the reservoir.

30 Claims, 6 Drawing Figures

U.S. Patent  Nov. 23, 1982  Sheet 1 of 3  4,360,019
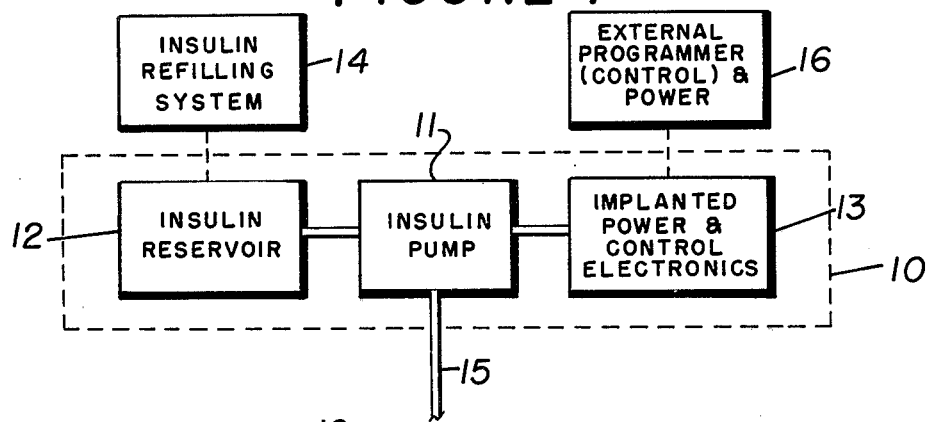
FIGURE 1
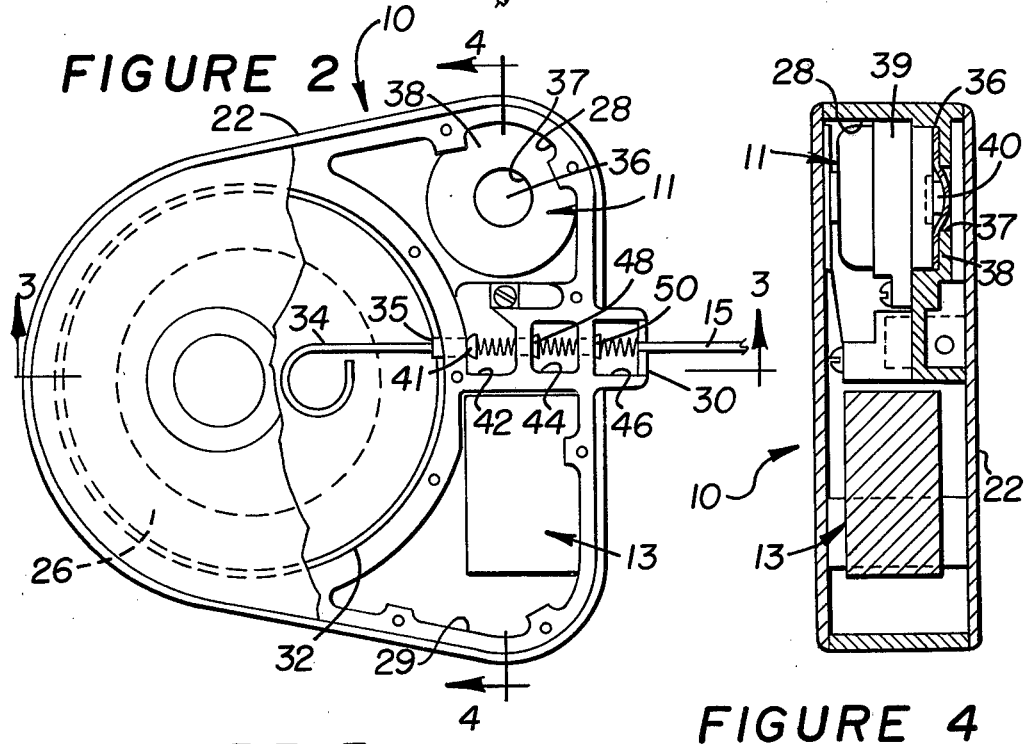
FIGURE 2
FIGURE 4
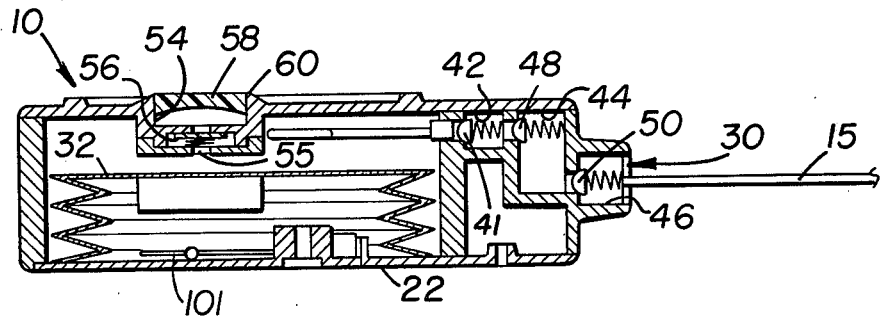
FIGURE 3

IMPLANTABLE INFUSION DEVICE

This application is a continuation-in-part of U.S. application Ser. No. 015,927 filed Feb. 28, 1979, now U.S. Pat. No. 4,265,241.

The present invention relates to drug delivery systems and more particularly to drug infusion devices which are implanted within the body of a patient.

Various types of drug delivery systems are well known in the prior art. Possibly the most common of these systems has been employed for the delivery of drugs to bedridden patients using an elevated container with a valve controlling the drip rate of the drug into a tube coupled with a needle inserted into the patient's body. With such a system, the flow rate may be controlled by means of the valve and may be readily monitored by visual observation of the drip rate. These systems present a number of problems, not the least of which is their limitation for use only with bedridden patients.

Other types of drug delivery systems are also known which employ various types of the flow control devices. For example, a drug may be delivered by operation of a low volume pump. All of these systems as employed within the prior art have exhibited numerous shortcomings. For example, most systems employing pumps have been rather large and have required substantial amounts of power for proper operation. In addition, these devices are typically limited to use with bedridden patients.

Certainly drug delivery systems have been considered for complete implantation within the body of a patient. Possibly, the most common type of device employed in this manner in the prior art has included a permeable membrane for controlled diffusion of a drug into the body from a suitable reservoir. However, such devices are limited in application primarily since the rate at which the drug is delivered to the body is completely dependent upon the rate of diffusion through the permeable membrane. Once the device is implanted within the body, external control over the device is no longer possible. Accordingly, the rate of drug delivery to the body may be affected by differing conditions within the body. In addition, such systems make no provisions for the adjustment of the rate or time interval for drug delivery, nor can the delivery rate be easily varied.

This invention relates to drug delivery systems and, more particularly, to a drug infusion system incorporating an infusion device which is implantable within the body of a patient.

The foregoing shortcomings of conventional drug infusion systems become acute in connection with drugs such as insulin, for which the bodies need may vary significantly over short periods of time. For example, the best presently available treatment for insulin-requiring diabetes management is to inject a bolus of fast-acting insulin before each meal, thereby simulating the normal physiological insulin release mechanism. Such a regimen requires four to six subcutaneous injections daily, a procedure unacceptable to most diabetics. A compromise used by many patients involves the administration of a mixture of rapidly and more slowly acting insulin subcutaneously twice a day.

The difficulties associated with the development of an acceptable glucose sensor have caused investigators to focus their attention on "open-loop" insulin delivery systems. Over the last five years a number of "open-loop" insulin delivery systems have been described in the literature. A few of these "open-loop" delivery systems were implantable (only one implanted in man), most were portable and extracorporeal, and some were barely mobile. They employed a variety of pumping mechanisms and energy sources. Most of the systems provided two rates of insulin delivery, a basal rate and a preprandial or postprandial (before or after eating) rate. Some systems were preprogrammed, based on measured diurnal insulin reqirements and some were flexible, allowing some adjustment of the delivery rates. Access for most systems (extracorporeal) was via the peripheral venous system, while in the implanted systems, a larger vein was used. Two systems used subcutaneous infusion in the anterior abdominal wall. Intraperitoneal delivery of insulin was explored by one of the investigators and has been reported by others. This route may result in a more physiological absorption with delivery of more insulin directly into the portal system. On the other hand, at least one study has failed to show a significant difference between intraportal and peripheral venous delivery of insulin.

All investigators found improved control of blood glucose with the "open-loop" systems. As might be expected, each system has advantages and disadvantages (in some cases insurmountable). None of the described systems is ideal in all its aspects. Only two of the reported systems are inherently implantable. Considerations of safety, infection, patient self-image and convenience make implantation of such a device mandatory for long-term (permanent) application in the control of insulin-dependent diabetics. Finally, the availability of a safe, reliable, durable, cosmetically acceptable and implantable "open-loop" insulin delivery system, with appropriate functional characteristics, would significantly improve glycemic control in the diabetic, and potentially increase life expectancy while decreasing morbidity.

An effective, safe and implantable device of high reliability and long life is shown and described in co-pending U.S. Application Serial No. 15,927. This device satisfies many of the basic requirements suggested above. However, the use of such concepts in a system which will functionally replace the beta-cell of the pancreas is not completely set forth.

Accordingly, it is an object of the present invention to provide an improved, effective, and safe implantable drug infusion device of the general type shown and described in U.S. Patent Application Ser. No. 15,927.

Another and more general object of the invention is to provide a highly reliable and versatile drug delivery system utilizing an implanted infusion device.

A further object of the invention is to provide a drug delivery system utilizing an implantable infusion device wherein the implanted device has a long life and functionally replaces the beta cell of the pancreas in an insulin-dependent diabetic.

Other objects of the invention will become apparent to those skilled in the art from the following description, taken in connection with the accompanying drawings wherein:

FIG. 1 is a block diagram of the drug delivery system of the invention;

FIG. 2 is a top plan view with the cover partially removed, of an implantable insulin device constructed in accordance with the invention;

FIG. 3 is a sectional view taken along the line 3—3 of FIG. 2;

FIG. 4 is a sectional view taken along the line 4—4 of FIG. 2;

Figure 5:
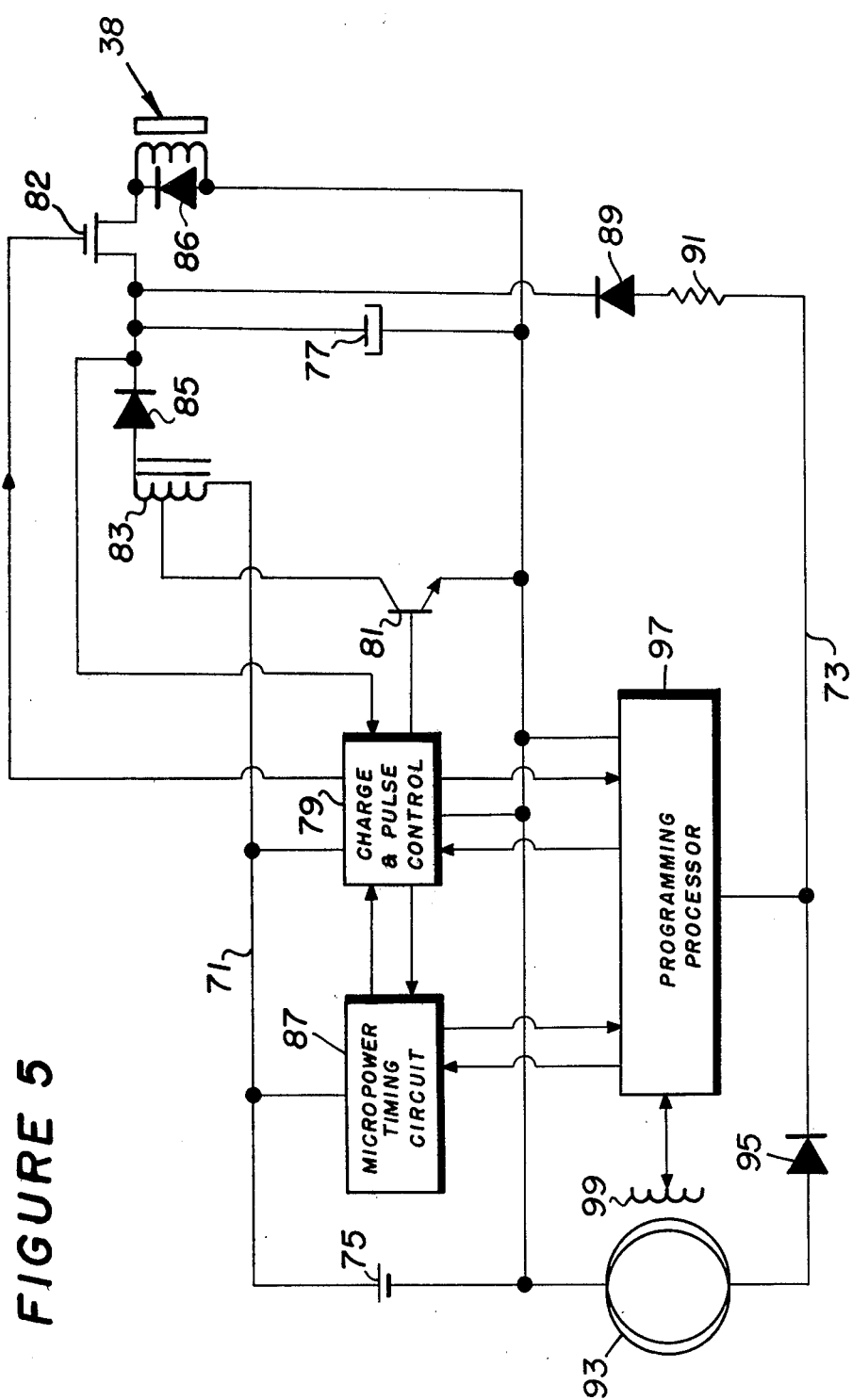
FIG. 5 is a schematic block diagram of the electrical configuration of the implantable insulin device of FIGS. 2 through 4.

Very generally, the drug delivery system of the invention includes an implantable infusion device comprising a housing for the device which is completely implantable within the body of a patient, a reservoir arranged in said housing for containing a predetermined drug, catheter means for connecting said reservoir with a portion of the body to which the drug is to be delivered, and actuating means operable for causing a flow of a precise dosage of the selected drug from the reservoir through the catheter means to the body portion. The actuating means include a pump and means for powering and controlling the pump in accordance with a preselected dosage profile. An external controller device is provided which includes means for altering the internal control profile, means for providing a dosage profile under external control, and means for providing externally originating power to the internal pump.

Referring now more particularly to the drawings, the proposed system is an implantable drug delivery system capable of providing two delivery rates. These rates are a basal rate and a bolus rate, each of which can be varied independently over wide ranges by the use of an extra corporeal programmer. A block diagram of the system is shown in FIG. 1. The major subsystems are the implantable device 10 including the insulin pump 11, the insulin reservoir 12, the implanted power and control system 13, the refilling system 14, the delivery catheter 15, and the extracorporeal (external) programmer and power system 16. The system is described below in connection with insulin delivery, but it will be apparent to those skilled in the art that the invention may be used with other drugs as well.

The basic concept involves the use of a positive displacement pump 11 of fixed stroke volume, the two delivery modes (e.g. basal and post-prandial) being achieved by an appropriate time sequence of pump actuation. The external programmer is designed to permit adjustment of both delivery rates and adjustment of the duration of the delivery rates. The implanted control circuit (and battery) automatically provide a programmed train of pump pulses at a frequency appropriate to the basal requirements. At the time of a meal, the external (palm-sized) programmer/power unit is placed over the subcutaneously implanted system and a predetermined insulin dose entered by means of a suitable key pad, not shown. The extracorporeal unit is inductively coupled to the implanted module and overrides the internal circuit, instructing the pump to deliver the selected amount of insulin with a series of pump pulses. The energy for these post-prandial pulses is transmitted transcutaneously, reserving the implanted battery for basal rate delivery.

For example, if a pump stroke volume of 2.5 mm$^3$ is chosen, and a basal rate of 12 units/day (0.5 u/hr) and post-prandial delivery of 8 units are desired, then with U-100 insulin, one pulse will be delivered automatically every thirty minutes and 32 pulses will be delivered postprandially. If a more continuous basal infusion is desired, a smaller stroke volume can be chosen, or a more dilute concentration of insulin utilized. For this example, use of U-40 insulin would result in the delivery of 0.1 units every twelve minutes to achieve the desired basal rate.

The combination of a positive displacement pump of fixed displacement with the type of digital (frequency of actuation) control described, results in a simple, accurate delivery system of extreme flexibility. Complete external control of the drug delivery profile can be achieved.

In describing the implantable device 10 of FIGS. 2–4 in detail, having reference to those FIGURES, the implantable infusion device is generally indicated at 10 and includes a rigid housing 22 preferably formed from stainless steel or titanium. The stainless steel or titanium housing 22 may be encased with a sheath (not shown) of a material designed for compatibility with the body, preferably a biocompatible polymer such as silicone rubber or polyurethane.

The interior of the housing 22 is generally divided into four regions including a reservoir portion 26, a pumping chamber portion 28, an electronics chamber portion 29 and an outlet portion 30 arranged for communication with the catheter 15 which is disposed outside of the housing 22. The entire housing may be shaped in order to better adapt the device to the body configuration when it is implanted.

The reservoir portion 26 of the device is separately formed by the housing 22 and further includes a variable volume bellows-type expansion chamber 32. An inlet tube 34 extends into the reservoir chamber portion 26 through an inlet port 35 and is looped at its end so that it terminates a short distance from the side of the straight portion of the tube. This distance is selected to be smaller than the diameter of any air bubbles that might form in the reservoir, thus blocking their entry into the tube. As an alternative, a suitable filter could be used. The tube 34 communicates with an appendage 42 of the pumping chamber portion 28 through a spring biased check valve 41. The pump 11 is also located in the pumping chamber 28, isolated from insulin therein by a diaphragm 36 extending across an opening 37 in a plate 38.

When the pump 11 is activated, insulin in the pump chamber 28 is pressurized by the elastomeric diaphragm 36, which is driven by a small solenoid 39 via a plunger 40. The fluid pressure opens multiple, redundant outlet valves, 48 and 50 and exits through the catheter 15 to the delivery site. The insulin is prevented from flowing back into the reservoir by the valve 41. All the valves are spring-loaded in the normally closed position. The stroke volume is determined by the diameter of the diaphragm and the stroke length of the solenoid armature. When the solenoid completes its stroke, the current pulse is turned off, and a spring returns the armature to its initial position. During the return stroke, insulin from the reservoir flows through the inlet port 35 to fill the pump chamber 28. The pump is then ready to be activated again. An alternative to the elastomeric pump diaphragm is a small metal diaphragm in the form of a bellows. Both approaches have been extensively tested and have presented no problems.

The housing 22 also includes internal structure forming a plurality of outlet chambers providing serial communication between the appendage 42 of the pumping chamber 28 and the catheter 15. The outlet chambers are indicated in FIG. 3, respectively at 44 and 46, the outlet chamber 46 being a final chamber which is in direct communication with the catheter 15. The separate outlet check valves 48 and 50, respectively, regulate communication of a drug from the appendage 42 of the pumping chamber 28 into the first outlet chamber 44, from the outlet chamber 44 into the next chamber 46.

The choice of the stroke volume, insulin concentration and frequency of actuation determine the actual insulin delivery to the patient. Once the device is implanted, the stroke volume is fixed; however, the other two variables (insulin concentration and frequency of actuation) can be readily adjusted to result in any desired insulin delivery profile. This flexibility and total external control of the delivery profile, as described below, provide a major advantage in the attempt to maintain euglycemia.

On the same side of the device, the housing 22 forms an additional opening 54 through which the drug supply within the chamber 26 may be replenished. To permit the fluid drug to be injected into the reservoir while preventing the drug from escaping out of the reservoir through the opening 59, a resealable septum 58 is provided in the opening 54. A check valve 56 is arranged within the opening 54, to control the flow of fluid from the opening 54 into the chamber 26 through an orifice 55. A needle may be inserted through the skin and the septum 58 for injecting a fresh supply of drug into the space between the septum 58 and the valve 56. From this space, the fluid passes into the chamber 26 through the orifice 55. When a drug is thus injected, the pressure opens the check valve 56 to cause the drug to flow into the reservoir. Upon restriction of the needle, the opening 54 is again closed by the check valve 56 so that the drug may be supplied to the body only by proper operation of the pump as described above. The housing 12 is also formed with an annular ridge 60 surrounding the opening 54 in order to assist in location of the opening 54 for injection of the drug into the reservoir.

The insulin reservoir 26 and the expansion chamber 32 are shown most clearly in FIG. 3. The reservoir has a typical capacity of 15 ml. Since the delivery system has a rigid sealed housing, some means must be provided to maintain a constant pressure in the space behind the insulin reservoir as the reservoir depletes. This is accomplished by the expansion chamber 32 which is in the form of a welded metal bellows.

The expansion chamber is filled with a suitable fluid, for example, a saturated vapor mixture of Freon 113 and Freon 11, which maintains a constant pressure, even with a 20 ml volume variation, as long as a constant temperature is maintained. Since the device is implanted in the body, temperature of the Freon vapor should be relatively constant. Thus, the expansion chamber pressure variation is essentially constant throughout the volume change of the reservoir. Any variation is typically less than 1 psi and is caused primarily by residual air trapped in the expansion chamber during the filling procedure. Suitable assembly procedures can eliminate this variation.

The metal bellows itself contributes slightly to the pressure variation, since it has a characteristic spring constant which results in, typically, a 0.3 psi change. The bellows can be chosen so as to cause a slight negative or positive pressure change depending on whether it is fabricated with closed or open convolutions.

There is an important distinction between this concept, which maintains a "selected" constant pressure behind the insulin reservoir, and other concepts where a fluorocarbon is used to maintain a high pressure in the insulin reservoir, thereby providing the energy to deliver the fluid. In the concept of the present invention, the reservoir is kept at slightly less than atmospheric pressure (e.g. −1 to −2 psi gauge i.e. negative gauge pressure), and the energy for fluid delivery is provided by the solenoid. When the solenoid plunger (or pump diaphragm) retracts, its motion causes the volume of the pump chamber to increase, thereby decreasing the fluid pressure in the pump chamber. This in turn causes the inlet valve to open. Fluid from the reservoir is drawn into the pump chamber and the inlet valve closes at the end of diaphragm retraction. When the solenoid plunger or diaphragm is advanced into the chamber, the pressure inside the chamber rises. The inlet valve remains closed (because of the positive pressure inside the chamber) while the outlet valve opens when the pressure inside the chamber exceeds the outlet valve preload pressure of about 12 psig. At the end of the ejection stroke, the pressure inside the pump chamber decreases causing the outflow valve to shut. Then as the plunger retracts, the cycle repeats itself as described earlier.

The energy for both the filling of the pump chamber and the delivery of the drug through the catheter are provided by the solenoid and not the expansion chamber. The volume delivered is constant and is positively displaced by the pump diaphragm motion, resulting in high accuracy and insensitivity to both inflow and outflow pressures. A change in the reservoir pressure does not, to first order, affect the pump stroke, since it is the plunger motion that determines the degree of pump fill and eject. Consequently, reservoir pressure is chosen to be slightly less than atmospheric (or negative psig). The pump will function with negative or positive gauge pressures as long as the inlet and outlet valve spring preloads (valve opening pressures) are appropriately selected.

A key advantage of this design stems directly from holding the insulin or drug reservoir at less than atmospheric pressure. In the event of any valve failures (either the redundant outlet valves or inlet valves or even all the valves) no insulin or other drug will leak out of the system. In any drug reservoir at higher than atmospheric pressure, valve failures would result in a dangerous uncontrolled delivery of the drug to the patient.

Finally, with any saturated vapor system, the effects of ambient temperature and pressure must be examined. As the temperature changes (under febrile conditions) the saturated vapor pressure will change and, consequently, the pressure in the insulin reservoir will also change. With changes in ambient pressure (e.g. an aircraft cabin is not fully pressurized to sea level) a pressure differential will exist between ambient pressure and reservoir pressure. In both instances, a pressure imbalance is created. However, as discussed earlier, the present (positive displacement) concept is insensitive to these changes, since filling and ejection are controlled by plunger motion. This may be contrasted by the effect on a system which relies on a pressurized reservoir as an energy source for delivery, which is quite severe with increases in delivery of up to 100% under certain conditions.

The position of the bellows 32 separating the insulin in the reservoir 26 is monitored by a simple capacitive position transducer designed into the expansion chamber. Consequently, the amount of insulin remaining in the reservoir can be determined at any time by using the external programmer module described below to interrogate the implanted transducer.

It is anticipated that the reservoir will be replenished whenever it is depleted to about 25% of its initial volume. A pressure transducer tap may be utilized with a conventional syringe and needle to monitor filling and avoid overfill. It is desirable that care be taken to purge all the air out of the refilling system. If the filling syringe is held vertically, any air in the refilling system will migrate away from the needle. The syringe may contain more insulin than is required so that it need not be emptied completely.

Two methods are available to determine that the insulin reservoir is full. If both are utilized, one serves as a cross-check against the other. Before initiating the refill procedure, the external programmer module described below is used to determine the insulin reservoir volume. This provides a direct measure of the volume of insulin required to fill the reservoir. The refill syringe is then used, as described above, to slowly fill the reservoir while constantly monitoring the filling pressure. Because the outlet valves 48 and 50 are preloaded to a relatively high pressure (e.g. 12 psig), the expansion chamber bellows (resistance $<<1$ psig) progressively compress. As the reservoir fills, the reservoir pressure (as indicated by the pressure gauge) will remain at a pressure less than 1 psig until the reservoir is completely full and the pressure rises sharply. The syringe is then withdrawn, completing the procedure. The sharp rise in pressure when the reservoir is full should occur at the volume predicted by the measurement with the implanted capacitive transducer.

The filling procedure can be simplified, if necessary, by replacing the pressure transducer with a preloaded relief valve set to about 3 psig. With this modification, the sharp pressure rise at the end of fill will limit at 3 psig, when the relief valve preload is reached. Excess insulin will then flow out harmlessly through the valved side tube. The outlet valve within the pump (set to 12 psig) will never open, so the reservoir cannot be overfilled.

The elastomeric (for example silicone rubber) refill plug (septum) is a critical component, since it must seal the hypodermic needle during the refill cycle, and continue to do so even after many punctures. There must also be no leakage over the long period of implantation. If the plug is designed to have a radial compression when inserted into the top cover, this radial compression will provide a better seal around the needle during refilling, and also seals existing puncture holes more effectively. As an additional safety feature, the redundant valve 56 is open only during filling, otherwise isolating the septum from the insulin reservoir and greatly minimizing the risk of insulin leakage through the plug.

The valves in the present invention may be made either entirely elastomeric (silicone or polyurethane) or from a plastic material with an elastomeric contact surface. Consequently, the valves are very light and responsive. Furthermore, each valve is spring-loaded against its seal. There are two outlet valves, in series, to provide redundancy. The outlet valves may be preloaded, for example, to an opening pressure of 12 psig. The inlet valve may be lightly preloaded, for example, to a pressure of 0.5 psig.

The preceding sections described several features which ensure failsafe operation. In addition, the overall system has been designed to have high reliability. The pump is inherently reliable because of its simplicity; there is only one moving part in the actuation system (the solenoid armature).

The electronics in the system of the invention provide two distinct functions. The first, or basal function is maintained by the electronics contained within the implanted insulin delivery device and is a pre-programmed rate of pump operation independent of extracorporeal power or control. In this mode, the implanted electronics must exhibit extremely high resistance to electromagnetic interferences (EMI) which might alter the preset time interval, or even cause supernumerary pump strokes. Preferably, this circuit also provides for feedback verification of the pump's mechanical function. When the battery, which powers the basal mode, nears exhaustion, degradation of basal pumping function occurs in an orderly fashion and includes a means of signaling the patient of this occurrence when the extracorporeal programming unit is next employed.

The second function, or bolus mode, is markedly different. The extracorporeal programmer described below is placed over the subcutaneously implanted insulin delivery device in such a way as to facilitate communication to and from the implanted unit by means of induction coils. This scheme is similar to that normally employed in the case of programmable implanted pacemakers, nerve stimulators and the like. The flat cylindrical shape of the insulin reservoir is well suited to serve as a substrate for such an induction coil. Since the power level required even for a rapid succession of pump strokes is less than a watt, it is advantageous to also employ this inductive coupling for power transfer in the bolus mode. At the power level involved, this provision does not complicate or enlarge the design of the induction loop. As elaborated later, this power transmission mode also reduces the likelihood of EMI during implanted device programming or read-back, since the information transmission can take place at a relatively high energy level.

The bi-modal energy supply described above leads to a circuit design concept for the implanted device which includes only one sizeable component other than the primary lithium battery and has a low parts count. Furthermore, many of the needed fail-safe features are inherent characteristics of the design. Again, the key concept underlying this circuit approach is separation of the simple basal function with its stringent power consumption requirement from the more sophisticated and higher power performance in the bolus and "reprogramming" mode.

Only simple demands are made on the basal control element. It must accept and store a pulse interval transmitted in a serial mode from the extracorporeal programmer; it must continue to generate pump strokes at this interval, verify their occurrence and give warning—during the next programmer interface—of pump malfunction or impending battery failure. Operation must degrade predictably without the possibility of increased pumping rate in the event of sudden battery failure.

In contrast, the extracorporeal interface is expected to perform many more functions and do so more rapidly. It must continually verify the adequacy of the inductive coupling for both power and data transmission, and signal this to the programmer. In the externally pulsed mode especially, it is vital to provide for feedback verification of physical pump operation. These periods, also, are the only time when the user can be apprised of abnormal conditions, such as discharge of the internal battery or depletion of the insulin reservoir.

The implanted circuit is shown in FIG. 5. In keeping with the dual-power mode philosophy, two separate DC voltage supplies are involved. Each power bus 71 and 73 energizes only those circuits which are associated with the functions of that mode, basal and bolus, respectively. If a lithium battery is used for the primary battery 75, its bus voltage will be approximately 3.6 volts for a single cell (series cells are undesirable for reliability reasons). Because the long-life primary battery would not provide the high peak currents necessary to energize the solenoid 38, the pulse energy is stored in a capacitor 77. As shown, a flyback type DC-to-DC converter charges this capacitor to a voltage matching the solenoid requirement, e.g. 15 volts. As shown, the circuit includes a charge and pulse control logic chip 79, a control transistor 81, and a flyback transformer 83 connected to the capacitor 77 through a diode 85. A diode 86 is connected across the coil of the solenoid 38.

For maximum stored energy density at low voltage, an electrolytic capacitor is used. To avoid power loss due to leakage currents in this type of capacitor, the capacitor is charged only just prior to delivery of a pulse. The capacitor is the only sizeable discrete component in the implanted circuit. Because the charging power level and even the discharge current are very small, the transformer and switching semiconductors are insignificant in size. These discrete components, together with the logic chips, may be fabricated as a thick-film hybrid circuit. Such fabrication is readily achievable by conventional techniques in the semiconductor art. This design particularly simplifies the provision of a relatively low-level holding current to the solenoid 38, since after the capacitor has discharged, current from the battery 75 continues to flow through the charger transformer 83 to the solenoid 38 as long as the switching transistor 81 is kept on.

A programmable timer micro-circuit 87 energized directly from the battery 75, signals the charger when a pump stroke is required. The charger is then started and when full charge is detected, the pump stroke is initiated, by means of a switch 82. Thus, the timing circuit may be that of a digital alarm watch or interval timer, and the technology for fabricating these devices to have (for this system) negligible battery drain, is well established.

An external command can utilize the closed solenoid as a dummy load for testing the battery and the charging circuit's ability to charge the capacitor, by overriding its normal logic and observing the effect charger operation has on capacitor voltage.

During the externally powered bolus phase (the external unit is described below), a higher processing speed is desirable. A power carrier frequency of at least 50 kHz, and preferably 100 kHz or more, will induce a reasonable voltage per turn in a pickup loop 93 of only a few centimeters in diameter. Externally provided power is supplied across the capacitor 77 during the bolus mode through a diode 95 in series with the diode 89 and resistor 91.

Data transmission carriers are of comparable frequency for effective noise-free transmission. Data is received from and transmitted to the extracorporeal unit, described below, by the coil 93. The coil couples signals to and receives signals from a processor 97, for processing the externally programmed information, by means of a transformer 99. To avoid a multiplicity of modulator and demodulator components, a processor clock rate in the MHz range may be used in the processor 97 to enable it to detect and generate these frequencies. Its power consumption will consequently be relatively high, but this power is supplied only transcutaneously and non-invasively.

In FIG. 5, rectification of the pickup loop power signal by the diodes 89 and 95, in series with the resistor 91, produces 15 volts. This is used to charge the pulse capacitor 77 directly, and the internal charger transformer 83 is not employed at all in the bolus mode. Thus, this mode can be activated normally even if the internal battery, timing circuit or charger malfunction. The series resistor 91 provides, after capacitor discharge, a solenoid holding current slightly greater than that furnished from the internal battery, so that the charger diode 85 does not conduct and no holding current is drawn from the battery 75.

Running time in the basal timing circuit and interval time are transferred to the external programming processor in a parallel output format, as would drive a watch display. The data are then converted by the processor to a serial format for transmission to the extracorporeal programmer. In contrast, interval re-programming data entering the "basal" timing circuit, are in serial format. The use of a single data line here simplifies inhibiting this bus while the external processor is powering up and down. As FIG. 5 shows, only two such input lines must be thus protected.

A relatively high power level can be used for data transmission to minimize the possibility of electromagnetic interference. Its low power level makes the "basal" timing circuit potentially the most vulnerable. Here the dual control concept provides a high measure of inherent security. Until full power is present in the external programming processor and an enabling code has been received and acknowledged, no signal can be transmitted to the timing circuit. This principle, the same as that used in electronic entry locks, completely isolates the "basal" timer from exogenous interference received on the pickup coil. Direct pickup in the timer circuit is, of course, easily prevented by shielding.

It is possible to employ the power waveform itself to carry data in using a frequency shift method. For full duplex, simultaneous input and output transmission, internally generated "data out" frequencies may be chosen to avoid harmonics of the power frequency generated by the rectifier. For example, division of a 1 MHz internal clock by 11, 9, 7 and 5 give frequencies of 91, 111, 143 and 200 kHz, respectively. No harmonic of any of these frequencies below 1 MHz is within 10 kHz of any other. Such signals are readily generated and discriminated by simple logic.

In addition to those discussed above, further diagnostic and verification functions are readily implemented within this basic design concept. For example, solenoid armature motion can be distinguished by measuring persistence of solenoid coil current at the end of stroke and by its rate of rise at the start. Since the zero-gap inductance of the solenoid is many times greater than at full gap, a malfunction will manifest as an abnormality in one of these periods.

The time resolution required for these measurements is well within the capability of a processor operating with a MHz clock rate. The existence of this precisely determined, high-frequency carrier, also facilitates measurement of the quantity of insulin remaining in the reservoir. FIG. 5 shows the major electrical components of the system. The bellows 32 of FIGS. 2—4 can also be employed as a variable capacitor. In this embodiment, a fixed insulated plate 101 placed within the bellows, 1 mm from the closest approach of the movable diaphragm, exhibits a 3.5 pF capacitance change between full and empty reservoir conditions. Excited at 15 volts peak-to-peak at the 1 MHz clock frequency, this capacitance change produces an easily detectable 115 μA current shift. Sealed inside the gas-filled bellows, the capacitor plate 101 is completely shielded from external electrical interference.

Figure 6:
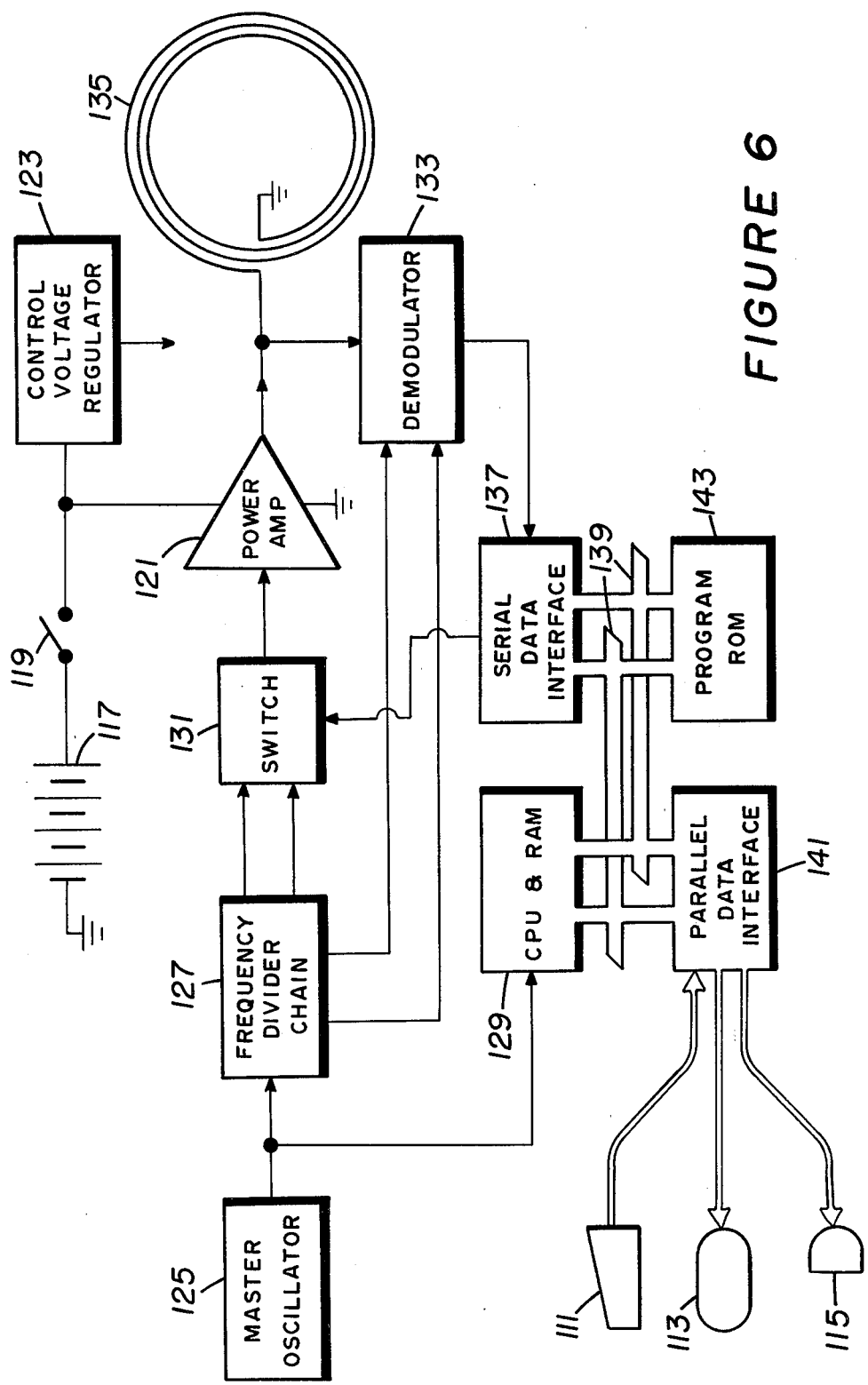
FIG. 6 is a schematic block diagram of an external control unit used in the drug delivery system of FIG. 1.

The extracorporeal programming package is fairly straightforward in design and construction, since space is not such a high premium and the battery can be readily renewed. The design of this package may follow closely the practice established for programmable pacemakers. The preferred design is shown in FIG. 6 and includes a numerical key pad 111 for entering the number of strokes (or units of insulin) desired in the bolus mode, for altering the "basal" time interval (rate) or for initiating any of the test functions enumerated earlier. Feedback verification of implanted device performance may take the form of alpha-numerical readout on a standard display, or go/no-go lights (LED) 113. For use by the visually impaired diabetic patient, the signaling format lends itself readily to the use of an audible signal output 115 both to signal establishment of proper inductive coupling and to convey data.

As may be seen from FIG. 6, the extracorporeal unit is powered by a battery 117 connected through a switch 119 to a power amplifier 121. Voltage regulation for the other components of the system is provided by a control voltage regulator 123. A master oscilator clock 125 is connected to a frequency divider chain 127 and to a CPU and RAM unit 129. The frequency divider chain provides output signals to a data switch 131 and to a demodulator 133. The switch controls the power amplifier 121 which is connected to a pancake coil 135. The demodulator output is applied to the serial data interface 137 which, in turn, is connected through the usual data and address buses 139 to the paralleled data interface unit 141 and to the PROM unit 143.

In operation of the extracorporeal unit, power and data are sent to the implanted unit through the pancake coil 135. Data from the implanted unit are also received by the pancake coil 135. Received data are applied to the demodulator 133 and from there to the serial data interface 137. The frequencies provided by the frequency divider chain 127 are selected to operate as multiplexed transmit and receive frequencies corresponding to the zero and 1 logical states. Selection of appropriate integrated circuit chips for performing the functions indicated by the blocks in the diagram of FIG. 6 may be made in accordance with known techniques.

By comparison with prior art approaches, the proposed linear reciprocating solenoid driver diaphragm pump offers an optimal mix of characteristics. It is a positive displacement pump with a well defined pump chamber geometry; consequently, its accuracy equals that of the syringe concept. Moreover, the pump chamber has no sliding seals. It does contain discrete valves; however, these are passive spring-loaded valves that require no actuating mechanism. The pumping energy is provided by a solenoid and delivery accuracy is not affected, to first order, by temperature or pressure. Furthermore, by maintaining the reservoir at a slightly negative gauge pressure, an uncontrolled release of insulin is impossible, even if all the valves should fail. The pump itself is mechanically very simple; with the exception of the passive valves, the entire pump mechanism consists of s single moving part—the solenoid plunger. Finally, the most significant benefit of the system is the digital (frequency of actuation) control of drug delivery—any desired basal and post-prandial delivery profiles can be easily achieved via the external programmer.

What is claimed is:

1. An implantable drug infusion device for delivering precisely regulated dosages of drugs into the body of a patient, comprising
    a housing for the infusion device which is implantable within the body of the patient,
    a reservoir for containing a selected drug,
    cathether means for connecting said reservoir with a portion of the body to which the drug is to be delivered,
    first actuating means including power means and control means internally contained within said infusion device housing for causing flow of the selected drug from said reservoir through said catheter means at a first dosage rate, and
    second actuating means responsive to non-invasive extracorporeal control means for causing flow of the selected drug from said reservoir through said catheter means at a second dosage rate determined by the extracorporeal control means, said second actuating means including means contained within said housing for receiving power from the extracorporeal control means through intact skin.

2. The implantable drug infusion device of claim 1 wherein said first actuating means is adapted for being overridden during the operation of said second actuating means in response to the extracorporeal control means.

3. The implantable drug infusion device of claim 2 wherein said internal control means for said first actuating means is responsive to the extracorporeal control means for adjusting the drug dosage delivered by said first actuating means.

4. The implantable drug infusion device of claim 1 wherein said internal control means for said first actuating means is responsive to the extracorporeal control means for adjusting the drug dosage delivered by said first actuating means.

5. The implantable drug infusion device of claim 1 wherein said reservoir includes means for maintaining a generally constant pressure within said reservoir which is less than atmospheric pressure, and further comprising pump means for supplying the drug from said reservoir to said catheter under control of said first and second actuating means.

6. The implantable drug infusion device of claim 5 wherein said pump means includes a reciprocating pump element and solenoid means for operating said pump element in response to said first and second actuating means, movement of said pump element in one direction drawing a drug supply from said reservoir into a pump chamber and movement of the pump element in the opposite direction causing the drug supply in the pump chamber to be delivered through said catheter means.

7. The implantable drug infusion device of claim 6 wherein said uniform pressurizing means within said reservoir means comprises an extensible and collapsible bellows forming a separate gas pressure chamber, said bellows including capacitive means for producing a signal corresponding to the volume of said reservoir.

8. The implantable drug infusion device of claim 1 further comprising drug outlet means arranged within said reservoir means for permitting the drug to flow from said reservoirs means while trapping bubbles within said reservoir means.

9. The implantable drug infusion device of claim 8 wherein said drug outlet means comprises a tube extending into said reservoir means and having an open end within said reservoir means spaced a distance from a surface within said reservoir means selected to prevent bubbles from entering the tube.

10. The implantable drug infusion device of claim 8 wherein said tube is bent back upon itself so that the open end of the tube is spaced slightly apart from a surface portion of the tube.

11. The implantable drug infusion device of claim 1 further comprising inlet means for permitting injection of a drug supply into said reservoir means while said infusion device is implanted within the body of the patient.

12. The implantable drug infusion device of claim 11 wherein said inlet means includes a penetrable, self-sealing membrane for allowing injection of a drug supply into said reservoir means and further comprising a redundant check valve means in series with said membrane for preventing escape of the drug supply from said reservoir through said inlet means.

13. The implantable drug infusion device of claim 1 wherein said reservoir means includes expansible and retractable means arranged therein for maintaining a generally uniform pressure within said reservoir when the drug supply within said reservoir is increased or decreased, said pressurizing means further being adapted to produce a sharp pressure rise within said reservoir when it is properly filled with a drug supply in order to produce a detectable pressure rise signal indicating that said reservoir is full.

14. The implantable drug infusion device of claim 1 wherein said first actuating means is adapted for delivery of the drug from said reservoir through said catheter at a basal rate, said second actuating means being responsive to the extracorporeal means for delivery of the drug from said reservoir through said catheter means at a bolus rate, said first actuating means being adapted to be overridden during operation of said second actuating means.

15. A drug infusion system for delivering precisely regulated dosages of drugs into the body of a patient, comprising
an implantable component including a housing which is implantable within the body of a patient, a reservoir for containing a selected drug, catheter means for connecting said reservoir with a portion of the body to which the drug is to be delivered, first actuating means including control means internally contained within said housing for causing flow of the selected drug from said reservoir through said catheter means at a first dosage rate, power receiving means, and second actuating means operable with power from said power receiving means for causing flow of the selected drug from said reservoir through said catheter means at a second dosage rate, and
an extracorporeal component including control means adapted for communication with the second actuating means when the infusion device is implanted within the body of a patient for establishing the second selected rate of drug flow and further including means for supplying power to said power receiving means.

16. The implantable drug infusion device of claim 15 wherein said extracorporeal control means further includes means for monitoring the drug supply level within said reservoir, means for monitoring the condition of said power source within said first actuating means, and means for monitoring delivery of said drug supply through said catheter means.

17. The drug infusion system of claim 15 wherein said extracorporeal component further comprises means for overriding said first actuating means during operation of said second actuating means in response to said extracorporeal control means.

18. The drug infusion system of claim 17 wherein said extracorporeal component further comprises means for adjusting the drug dosage rate established by said first actuating means.

19. The drug infusion system of claim 15 wherein said extracorporeal component further comprises means for adjusting the drug dosage rate established by said first actuating means.

20. The drug infusion system of claim 15 wherein said implantable component further comprises pump means for supplying the drug from said reservoir to said catheter under control of one of said first and second actuating means, said pump means including a reciprocating pump element operated by solenoid means in response to one of said first and second actuating means, movement of said pump element in one direction drawing a drug supply from said reservoir into a pump chamber and movement of the pump element in the opposite direction causing the drug supply in the pump chamber to be delivered through said catheter means.

21. The drug infusion system of claim 20 wherein said extracorporeal component further comprises means for monitoring operation of said pump means.

22. The drug infusion system of claim 15 wherein said reservoir means includes means for maintaining a generally constant pressure within said reservoir regardless of the amount of drug supply within said reservoir, said extracorporeal component including means for monitoring the drug supply within said reservoir.

23. The drug infusion system of claim 22 wherein said uniform pressurizing means within said reservoir comprises an extensible and collapsible bellows, said bellows including capacitive means for producing a signal corresponding to the volume of said reservoir, said monitoring means in said extracorporeal component being adapted for receiving said signal.

24. The drug infusion system of claim 15 further comprising a drug outlet means arranged within said reservoir for permitting the drug to flow from the reservoir while trapping bubbles within said reservoir.

25. The drug infusion system of claim 24 wherein said drug outlet means comprises a tube extending into said reservoir and having an open end within said reservoir spaced slightly apart from a surface to prevent bubbles from entering said tube.

26. The drug infusion system of claim 25 wherein said tube is bent back upon itself so that the open end of the tube is spaced slightly apart from a surface portion of the tube.

27. The drug infusion system of claim 15 wherein said implantable component further comprises inlet means for permitting injection of a drug supply into said reservoir while the implantable component is within the body of the patient.

28. The drug infusion system of claim 27 wherein said inlet means includes a penetrable, self-sealing membrane for allowing injection of a drug supply into said reservoir and further comprising a check valve means in series with said membrane for preventing escape of the drug supply from said reservoir through said inlet means.

29. The drug infusion system of claim 15 wherein said reservoir means includes expansible and retractable means arranged therein for maintaining a generally uniform pressure within said reservoir when the drug supply within said reservoir is increased or decreased, said pressurizing means further being adapted to produce a sharp pressure rise within said reservoir when it is properly filled with a drug supply in order to produce a detectable pressure rise signal indicating that said reservoir is full.

30. The drug infusion system of claim 15 wherein said first actuating means is adapted for delivery of the drug from said reservoir means through said catheter at a basal rate, said second actuating means being responsive to said extracorporeal means for delivery of the drug from said reservoir through said catheter means at a bolus rate, said extracorporeal control means including means for overriding said first actuating means during operation of said second actuating means.

* * * * *